United States Patent
Studin

(10) Patent No.: US 7,137,995 B2
(45) Date of Patent: Nov. 21, 2006

(54) BREAST IMPLANT INJECTOR AND METHOD OF USE

(75) Inventor: Joel R. Studin, Great Neck, NY (US)

(73) Assignee: JSM Licensing, LLC., Great Neck, NY (US)

( * ) Notice: Subject to any disclaimer, the term of this patent is extended or adjusted under 35 U.S.C. 154(b) by 60 days.

(21) Appl. No.: 10/789,030

(22) Filed: Mar. 1, 2004

(65) Prior Publication Data

US 2005/0192668 A1 Sep. 1, 2005

(51) Int. Cl.
*A61F 2/12* (2006.01)

(52) U.S. Cl. .............................. 623/8; 623/7; 604/500; 604/181

(58) Field of Classification Search .................. 604/68, 604/181, 183, 187, 195, 500, 510, 15, 27, 604/33, 36, 42, 48, 57, 72, 93.01, 218, 264, 604/164.05; 623/7, 8; *A61F 2/12*
See application file for complete search history.

(56) References Cited

U.S. PATENT DOCUMENTS

| | | | |
|---|---|---|---|
| 4,341,211 A * | 7/1982 | Kline | 604/514 |
| 4,498,902 A * | 2/1985 | Ash et al. | 604/164.05 |
| 4,643,733 A * | 2/1987 | Becker | 623/8 |
| 4,874,374 A * | 10/1989 | Kousai et al. | 604/164.05 |
| 4,955,906 A | 9/1990 | Coggins et al. | 623/8 |
| 5,201,779 A * | 4/1993 | Shiao | 606/91 |
| 5,258,026 A * | 11/1993 | Johnson et al. | 623/8 |
| 5,507,807 A * | 4/1996 | Shippert | 623/8 |
| 5,571,178 A | 11/1996 | Ledergerber | 623/8 |
| 5,723,006 A | 3/1998 | Ledergerber | 623/8 |
| 6,102,896 A * | 8/2000 | Roser | 604/218 |

* cited by examiner

*Primary Examiner*—Kevin C. Sirmons
*Assistant Examiner*—Andrew Gilbert
(74) *Attorney, Agent, or Firm*—Frenkel & Associates

(57) ABSTRACT

A breast implant injector device comprising a hollow guide cylinder having an open injection end and an opposed filling end, the cylinder having an elongated slot extending from the injection end toward the filling end, and an elongated plunger which can be pushed through the interior of the hollow cylinder. An unfilled breast implant can be inserted in the cylinder and a fill tube extending from the implant can extend from the interior of the cylinder through the elongated slot. Pushing the plunger through the cylinder pushes the implant through the open injection end, which can be directed into the open incision for injecting the implant therein.

6 Claims, 3 Drawing Sheets

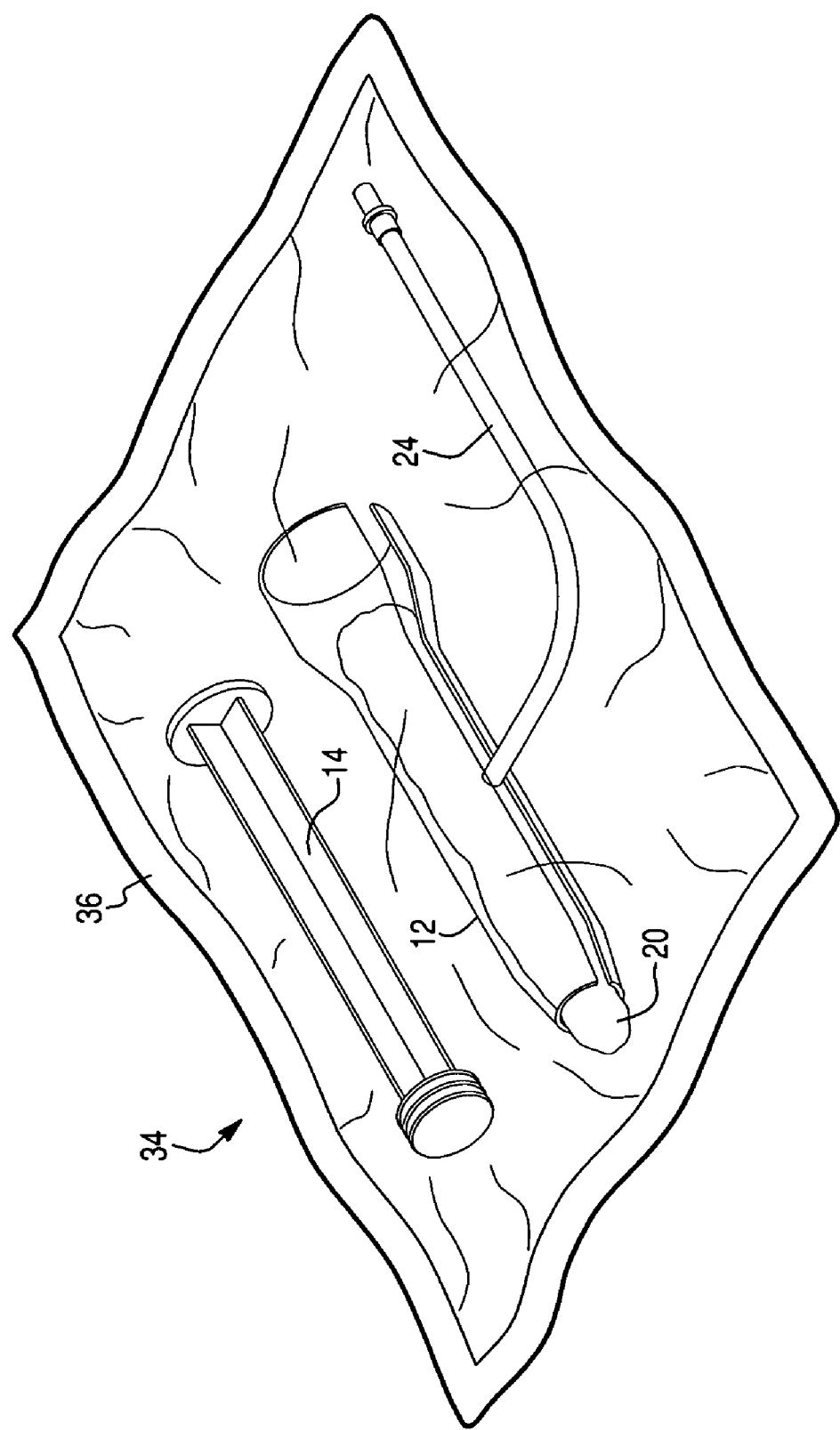

BREAST IMPLANT INJECTOR AND METHOD OF USE

FIELD OF THE INVENTION

The present invention relates to a device for injecting a breast implant into a surgically created body cavity.

BACKGROUND OF THE INVENTION

Reconstruction of the human breast involves introducing a fixed or changeable-volume sac-like silicone rubber structure into a body cavity surgically created to receive such an implant. The implants and coverings therefore are described, by way of illustration and not by limitation, in: Braumann U.S. Pat. No. 4,648,880; Hamas U.S. Pat. No. 4,531,244; and Ledergerber U.S. Pat. No. 4,955,907.

The usual skin incision is on the order of 3–8 centimeters in length and is stretched open with retractors to facilitate the introduction of the implant. In various surgical procedures, a breast implant is placed within the surgically formed body cavity for subsequent inflation and/or deflation with a fluid.

In plastic and reconstructive surgery, when a breast implant or tissue expander is placed in the dissected pocket, it is typically filled via a fill connector coupled to fill tubing which is attached to a filling material (e.g. saline solution) source.

There are currently three basic types of fill connectors used to connect the fluid source to the implant, the choice of which often depends on the implant and the particular surgical approach used. The first is a permanent attachment of the fill tubing to the implant. A common means for this attachment is to make a small opening within the body or shell of the implant and insert the tubing securing it by means of connecting materials such as sleeves, patch assemblies, adhesives or vulcanizing compounds.

The other two common connectors are for temporary attachment of the fill tubing to the implant by means of a valve in the implant which seals after the fill tubing is removed. One of these two temporary attachment means is most commonly used with saline-fill breast implant devices that include a diaphragm valve within the shell. The valve has an opening that requires a rigid male implement to be inserted in the opening thus opening the valve and allowing fluid transfer. This male implement is the fill tip end of the fill connector, which has on the opposite end one or more barbs which accept the flexible (e.g. silicone or vinyl) fill tubing. In use, the fill connector and fill tubing attach to the implant normal to the implant surface.

Since breast implants are usually placed into the body through incisions considerably smaller than the implant, it has always been a challenge to introduce them. With greatly increased friction at the interface between the surface of newer texturized implants and the wound margins (body tissue), it has become correspondingly more difficult to introduce these implants. Increased manipulation of both implants and patient tissue often results in trauma to both implants and patient tissue, thereby increasing the risk associated with the procedure both in terms of immediate consequences as well as delayed structural failure and the implications deriving therefrom. Postoperative infection has also been a troublesome consequence of the need to manipulate the implant into place. It has become a matter of some urgency to be able to introduce breast implants atraumatically.

SUMMARY OF THE INVENTION

A novel breast implant introducer is provided which has as its object the alleviation of the difficulty of introducing breast implants, and thus limiting greatly both the damage to implants and trauma to patient tissues. The breast implant introducer greatly reduces the need to manipulate the breast implant in to place in the formed body cavity, and as a consequence greatly reduces postoperative infection.

The breast implant introducer is a modified syringe including a hollow guide cylinder open at opposite ends and having an internal area capable of receiving an unfilled breast implant. An elongated plunger sized to fit within the interior of the guide cylinder through an opened end thereof is used to push the breast implant into place in the surgically created body cavity. The hollow cylinder includes along one side thereof an elongated slot to allow the fill tube connected to the breast implant to extend outside of the guide cylinder and move with the breast implant without kinking and without inhibiting the movement of the breast implant as it is injected from the guide cylinder into the body cavity. In as much as the surgeon contacts only the outside surface of the guide cylinder and the top of the plunger, risk of infection by transfer from the surgeon to the breast implant is substantially avoided.

BRIEF DESCRIPTION OF THE DRAWINGS

FIG. 5 is a perspective view of the breast implant injector of this invention packaged for sanitary use.

DETAILED DESCRIPTION OF THE INVENTION

Figure 1:
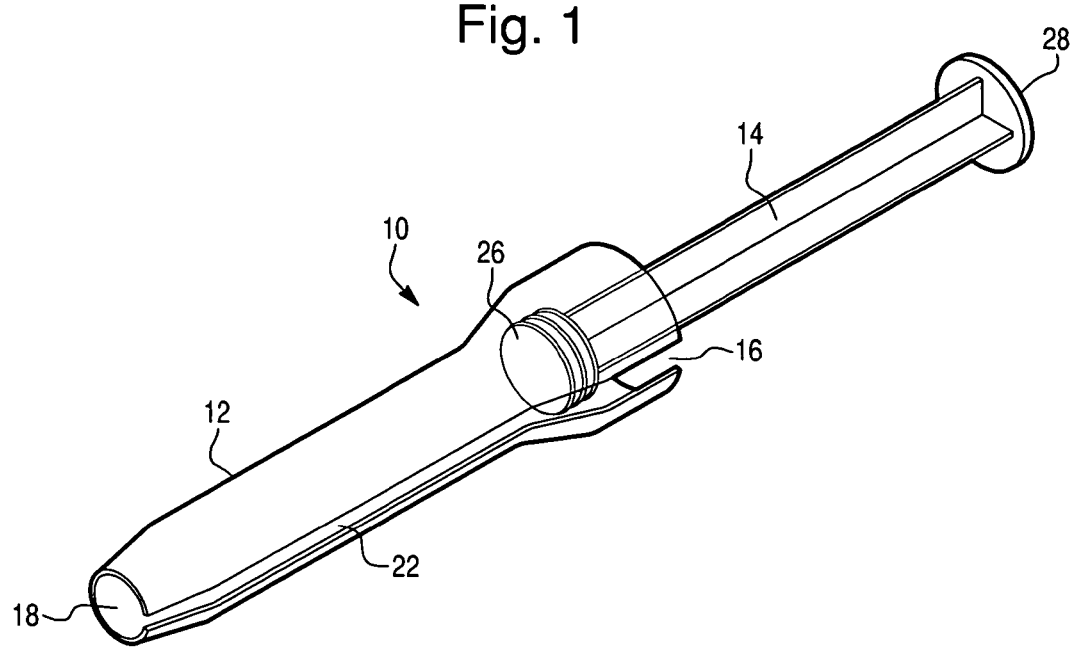
FIG. 1 is a perspective view of the breast implant injector of this invention.
Figure 2:
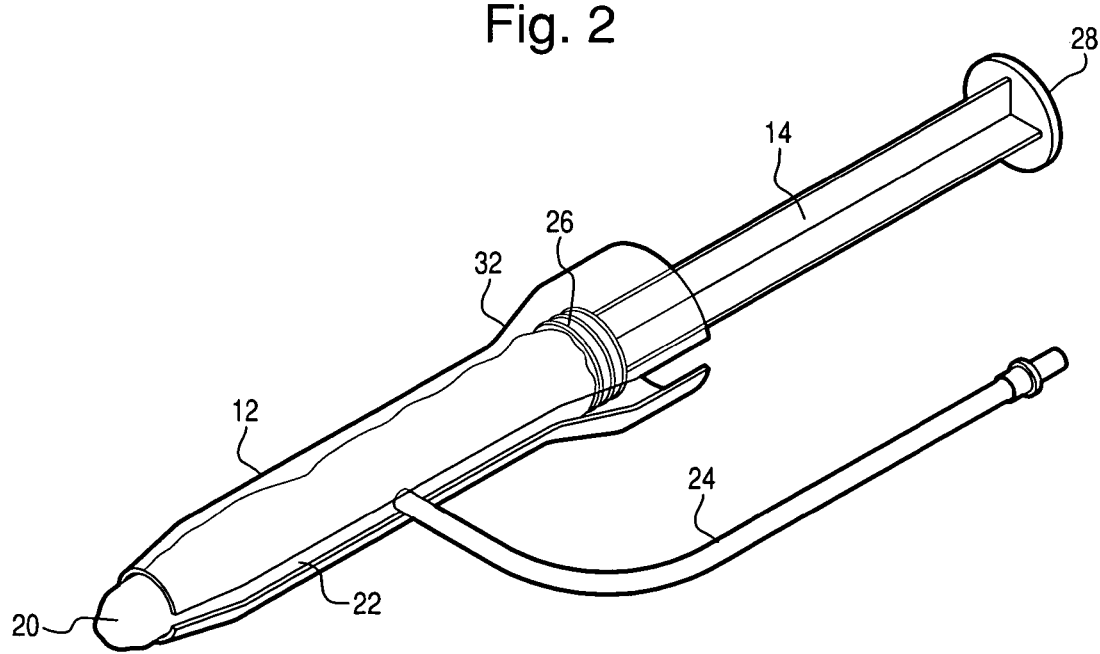
FIG. 2 is a perspective view of the breast implant injector of this invention showing the initial placement of the breast implant within the guide cylinder.
Figure 3:
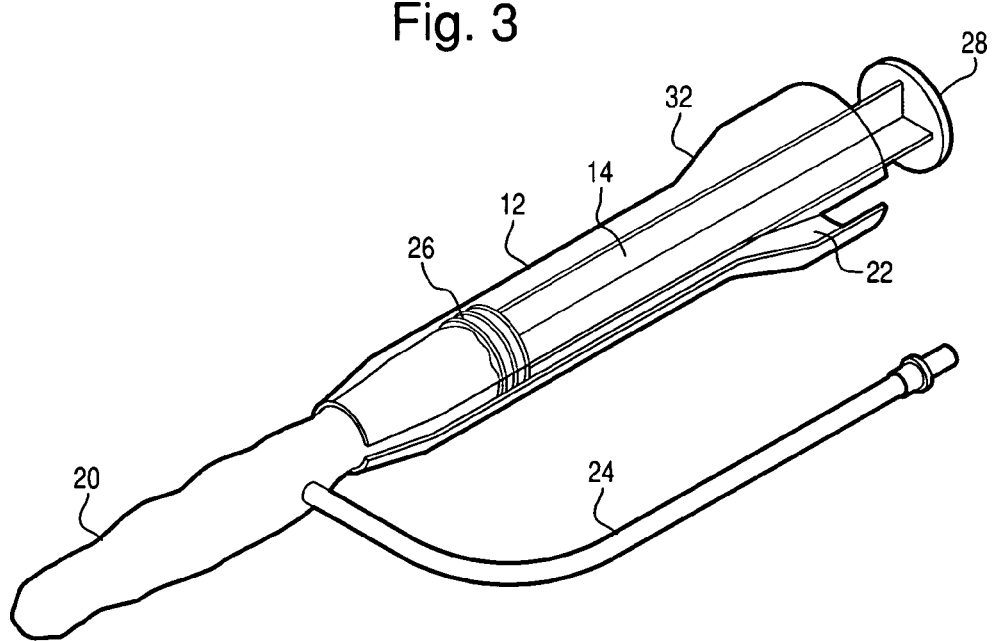
FIG. 3 is a perspective view of the breast implant injector showing the displacement of the implant from within the guide cylinder.

FIG. 1 of the drawings illustrates the implant injector 10 as comprised of a guide cylinder 12 and a plunger 14, slideable within and along the interior of the guide cylinder 12. The guide cylinder 12 is open at the opposed ends thereof including filling end 16 and opposed injection end 18 to allow the insertion of an unfilled breast implant 20 within cylinder 12 and the injection thereof out of cylinder 12, respectively, as shown in FIGS. 2 and 3. Along one side of guide cylinder 12 is an elongated slot 22 which is disposed from injection end 18, preferably, to filling end 16, to allow fill tube 24 of implant 20 to extend beyond the interior of guide cylinder 12 and allow passage of the unfilled breast implant 20 through the guide cylinder 12 in a smooth, uninterrupted manner. It is preferred that the guide cylinder 12 narrow adjacent to the injection end 18 to improve the guidance of the implant 20 into the body cavity or open incision during injection of the implant 20 from the interior of guide cylinder 12. Guide cylinder 12 can be formed of any material capable of forming a relatively rigid cylinder having an interior surface which is relatively smooth to not adversely impede the movement of the breast implant through the interior of the guide cylinder 12. Thus, glass, metal, ceramic, and plastic materials formed from synthetic resins such as polyacrylates, polyesters, polyamides, polyacetals, and the like are all acceptable to form the guide cylinder of this invention. The guide cylinder 12 should be relatively rigid and not easily bend once the unfilled breast implant 20 is inserted in the interior of the guide cylinder 12 and is pushed out through the open injection end 18 by means of plunger 14.

Plunger 14 is an elongated rod having a diameter which can fit within the interior of guide cylinder 12. Typically, the plunger 14 will have a flattened end 26 capable of providing sufficient surface contact with the breast implant 20 so as to push the implant 20 down the length of the guide cylinder 12 and out through open injection end 18. Opposite flattened end 26, plunger 14 will include an end 28 which provides sufficient surface area to allow the surgeon to push plunger 14 through guide cylinder 12 such as by the thumb of the surgeon as the guide cylinder 12 is held between two fingers. Thus, end 28 preferably provides a flat surface, as shown in FIGS. 1–3. The plunger 14 can also be made of glass, metal, ceramic, or any synthetic resin material which again forms a rigid plunger which will not easily bend upon the application of pressure at either or both ends of the plunger. If the plunger is too flexible, pressure at either end would bend the plunger and hinder the ejection of the breast implant 20 out of the open injection end 18 of guide cylinder 12.

FIGS. 2 and 3 illustrate the placement and movement of the breast implant 20 in and from the interior of guide cylinder 12. With the plunger removed from filling end 16, the implant 20 can be placed into the interior of guide cylinder 12 so that the fill tube 24 extends out through slot 22. Plunger 14 is then inserted into the open filling end 16 of guide cylinder 12 and is pushed toward open injection end 18. End 26 of plunger 14 pushes the breast implant 20 toward end 18 until implant 20 is ejected from the guide cylinder 12 through open injection end 18. The fill tube 24 of breast implant 20 does not get entangled with or hinder the movement of the breast implant 20 during passage through guide cylinder 12 since the fill tube 24 extends outside the guide cylinder 12 through elongated slot 22.

Figure 4:
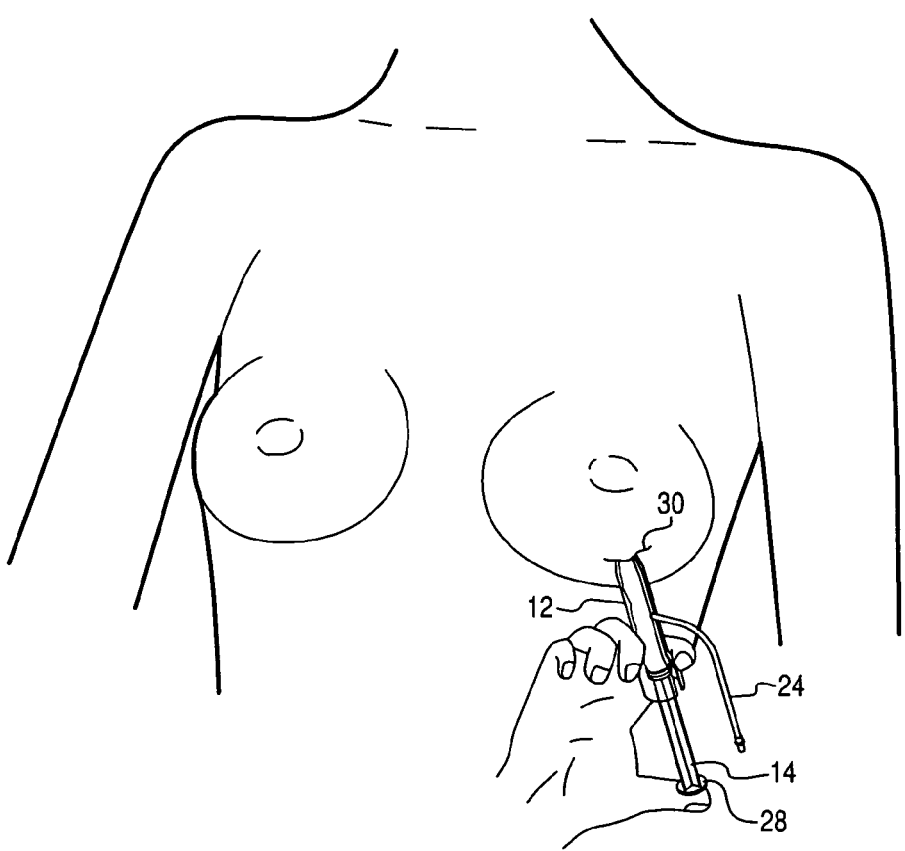
FIG. 4 is a schematic showing the use of the breast implant injector of this invention.

When mammoplasty is conducted using the present invention as illustrated in FIG. 4, the unfilled implant 20 is placed within the interior of guide cylinder 12, for example, through filling end 16. The fill tube 24 attached to implant 20 extends outside of guide cylinder 12 via slot 22. The injector 10 is inserted into the incision 30 in the skin of the patient so that the tip, i.e., injection end 18, of guide cylinder 12 is placed inside the incision 30. As illustrated in FIG. 4, the plunger 14 is placed into the open filling end 16 of guide cylinder 12 for pushing breast implant 20 through the cylinder 12 out through injection end 18 and positioned into the open body cavity through incision 30.

Referring to FIGS. 3 and 4, the surgeon can place the guide cylinder 12 between two fingers which grasp opposite sides on the outside of guide cylinder 12. Preferably, cylinder 12 has a widened portion or abutment 32 adjacent open end 16 to provide a location where the fingers of the surgeon can provide pressure and sufficient leverage upon pushing the plunger 14 into cylinder 12. The surgeon can then place the thumb of the same hand holding the cylinder 12 on the outer end 28 of plunger 14 and push the thumb and fingers holding the cylinder 12 toward each other to allow passage of plunger 14 through guide cylinder 12 while the plunger pushes the implant 20 through injection end 18 of cylinder 12 and into the open incision 30. As the implant 20 is being pushed through injection end 18, fill tube 24 is pushed along elongated slot 22 until the fill tube passes out of elongated slot 22 at end 18. During passage of the implant through the guide cylinder 12, the fill tube 24 does not impede the passage of the implant 20 such as by folding under the implant as can happen if the elongated slot 22 were not present. The surgeon can manipulate the injection end 18 of guide cylinder 12 to ensure that the implant 20 is properly in place without the need for manipulating the implant 20 with the fingers, which can often transfer unwanted microbes into the open body cavity and cause infection once the incision 30 is closed. After the operation, the used injector, produced at cheap cost, can, if desired, be disposed to completely stop infection caused by insufficient disinfection and repeated use. Therefore, the present invention is highly practical and safe. Once in place, the breast implant 20 can be filled, for example, with the desired saline composition at the desired level and the fill tube 24 removed. The implant 20 self seals once the fill tube 24 is removed, as known in the art.

With a novel configuration, the present invention allows a faster and more smooth operation compared to the prior art in the mammoplasty involving the insertion of the implant while there is the major time saving; furthermore, for cheap production cost and promoted production outputs, the injector of the present invention can be disposable to completely rule out the infection problem due to repeated use which requires the disinfection in the prior art. It is contemplated that a kit 34 containing the unfilled breast implant 20 placed within a guide cylinder 12 of this invention, and optionally containing the plunger 14, can be packaged together in a sanitary wrap 36 and opened when surgery is ready, again reducing the handling of the implant by the surgeon.

What is claimed is:

1. A method of inserting an unfilled breast implant into an opened incision, said breast implant including a fill tube extending therefrom, placing the unfilled breast implant in a hollow cylinder having opposed open ends, including an injection end and a filling end, said cylinder having an elongated slot disposed from said injection end extending toward said filling end, said fill tube extending from the interior of said cylinder through said elongated slot, pushing a plunger through said filling end of said cylinder, placing said injection end of said cylinder into said open incision, pushing said plunger through said cylinder so that said breast implant moves through said injection end and into said incision while said fill tube moves along said elongated slot toward said injection end.

2. The method of claim 1, wherein said breast implant is a fixed or changeable-volume sac.

3. The method of claim 1, wherein said injection end has a narrower diameter than the opposed filling end.

4. The method of claim 3, wherein said elongated slot extends entirely through and beyond said injection end toward said opposing filling end.

5. The method of claim 1, wherein said cylinder includes an outward abutment surface adjacent said filling end to provide a surface onto which increased finger pressure can be applied.

6. The method of claim 1, wherein said plunger has a flattened end so as to provide sufficient surface area to push an implant through said guide cylinder.

* * * * *